United States Patent
Jang

Patent Number: 5,948,016
Date of Patent: Sep. 7, 1999

[54] INTRAVASCULAR STENT WITH NON-PARALLEL SLOTS

[76] Inventor: G. David Jang, 30725 Fashion La., Redlands, Calif. 92374

[21] Appl. No.: 08/936,297

[22] Filed: Sep. 25, 1997

[51] Int. Cl.⁶ .................... A61F 2/06; A61F 2/04
[52] U.S. Cl. ............................................ 623/1; 623/12
[58] Field of Search ..................... 623/1, 11, 12; 606/192, 194, 195, 198

[56] References Cited

U.S. PATENT DOCUMENTS

| | | | |
|---|---|---|---|
| 4,994,071 | 2/1991 | MacGregor | 606/194 |
| 5,102,417 | 4/1992 | Palmaz . | |
| 5,389,106 | 2/1995 | Tower | 623/1 |
| 5,449,373 | 9/1995 | Pinchasik et al. . | |
| 5,545,210 | 8/1996 | Hess et al. . | |
| 5,591,197 | 1/1997 | Orth et al. . | |
| 5,593,442 | 1/1997 | Klein . | |
| 5,669,924 | 9/1997 | Shaknovich | 623/1 |
| 5,695,516 | 12/1997 | Fischell et al. . | |
| 5,697,971 | 12/1997 | Fischell et al. . | |
| 5,733,301 | 3/1998 | Forman | 606/192 |
| 5,772,864 | 6/1998 | Moller et al. | 623/1 |
| 5,776,161 | 7/1998 | Globerman . | |
| 5,776,183 | 7/1998 | Kanesake et al. . | |
| 5,810,872 | 9/1998 | Kanesaka et al. | 623/1 |
| 5,824,043 | 10/1998 | Cottone, Jr. | 606/195 |

FOREIGN PATENT DOCUMENTS

| | | |
|---|---|---|
| 0 587 197 A1 | 10/1991 | European Pat. Off. . |
| 606 165 A1 | 1/1994 | European Pat. Off. . |
| 679 372 A2 | 4/1995 | European Pat. Off. . |
| 0 709 067 A2 | 5/1996 | European Pat. Off. . |
| 43 03 181 A1 | 2/1993 | Germany . |
| 296 08 037 U1 | 5/1996 | Germany . |
| WO 96/03092 A1 | 2/1996 | WIPO . |
| WO 96/26689 | 9/1996 | WIPO . |
| WO 97/40780 | 11/1997 | WIPO . |
| WO 97/40781 | 11/1997 | WIPO . |

*Primary Examiner*—David H. Willse
*Assistant Examiner*—John M. Black
*Attorney, Agent, or Firm*—Wilson Sonsini Goodrich & Rosati

[57] ABSTRACT

A stent in a non-expanded state includes a first expansion column having a plurality of first expansion column slots that are formed of a plurality of first expansion struts. Substantially each first column expansion slot has a longitudinal axis. A second expansion column has a plurality of second expansion column slots that are formed of a plurality of second expansion struts. Substantially each second expansion column strut has a longitudinal axis. A first connecting strut column is formed of a plurality of first connecting struts. The first connecting strut column couples the first expansion column to the second expansion column. The first expansion column, second expansion column and the first connecting strut column form a first tubular structure with a longitudinal axis. The longitudinal axis of the first expansion column slots is non-parallel to the longitudinal axis of the first tubular structure.

20 Claims, 15 Drawing Sheets

INTRAVASCULAR STENT WITH NON-PARALLEL SLOTS

BACKGROUND OF THE INVENTION

1. Field of the Invention

This invention relates to intravascular stents, and more particularly to an intravascular stent which provides easy introduction through tortious sections of vessels.

2. Description of the Related Art

Angioplasty, either coronary or general vascular, has advanced to become the most effective means for revascularization of stenosed vessels. In the early 1980's, angioplasty first became available for clinical practice in the coronary artery, and has since proven an effective alterative to conventional bypass graft surgery. Balloon catheter dependent angioplasty has consistently proven to be the most reliable and practical interventional procedure. Other ancillary technologies such as laser based treatment, or directional or rotational arthrectomy, have proven to be either of limited effectiveness or dependent on balloon angioplasty for completion of the intended procedure. Restenosis following balloon-based angioplasty is the most serious drawback and is especially prevalent in the coronary artery system.

Many regimens have been designed to combat restenosis, with limited success, including laser based treatment and directional or rotational arthrectomy. Intravascular stenting, however, noticeably reduces the restenosis rate following angioplasty procedures. The procedure for intravascular stent placement typically involves pre-dilation of the target vessel using balloon angioplasty, followed by deployment of the stent, and expansion of the stent such that the dilated vessel walls are supported from the inside.

The intravascular stent functions as scaffolding for the lumen of a vessel. The scaffolding of the vessel walls by the stent serve to: (a) prevent elastic recoil of the dilated vessel wall, (b) eliminate residual stenosis of the vessel; a common occurrence in balloon angioplasty procedures, (c) maintain the diameter of the stented vessel segment slightly larger than the native unobstructed vessel segments proximal and distal the stented segment and (d) as indicated by the latest clinical data, lower the restenosis rate. Following an angioplasty procedure, the restenosis rate of stented vessels has proven significantly lower than for unstented or otherwise treated vessels; treatments include drug therapy and other methods mentioned previously.

Another benefit of vessel stenting is the potential reduction of emergency bypass surgery arising from angioplasty procedures. Stenting has proven to be effective in some cases for treating impending closure of a vessel during angioplasty. Stenting can also control and stabilize an unstable local intimal tear of a vessel caused by normal conduct during an angioplasty procedure. In some cases, an incomplete or less than optimal dilatation of a vessel lesion with balloon angioplasty can successfully be opened up with a stent implant.

Early in its development, the practice of stenting, especially in coronary arteries, had serious anticoagulation problems. However, anticoagulation techniques have since been developed and are becoming simpler and more effective. Better and easier to use regimens are continuously being introduced, including simple outpatient anticoagulation treatments, resulting in reduced hospital stays for stent patients.

An example of a conventional stent patent is U.S. Pat. No. 5,102,417 (hereafter the Palmaz Patent). The stent described in the Palmaz Patent consists of a series of elongated tubular members having a plurality of slots disposed substantially parallel to the longitudinal axis of the tubular members. The tubular members are connected by at least one flexible connector member.

The unexpanded tubular members of the Palmaz Patent are overly rigid so that practical application is limited to short lengths. Even with implementation of the multilink design with flexible connector members connecting a series of tubular members, longer stents can not navigate tortuous blood vessels. Furthermore, the rigidity of the unexpanded stent increases the risk of damaging vessels during insertion. Foreshortening of the stent during insertion complicates accurate placement of the stent and reduces the area that can be covered by the expanded stent. There is, further, no method of programming the stent diameter along its longitudinal axis to achieve a tapered expanded stent, and no method of reenforcement of stent ends or other regions is provided for.

Another example of a conventional stent patent is WO 96/03092, the Brun patent. The stent described in the Brun patent is formed of a tube having a patterned shape, which has first and second meander patterns. The even and odd first meander patterns are 180 degrees out of phase, with the odd patterns occurring between every two even patterns. The second meander patterns run perpendicular to the first meander patterns, along the axis of the tube.

Adjacent first meander patterns are connected by second meander patterns to form a generally uniform distributed pattern. The symmetrical arrangement with first and second meander patterns having sharp right angled bends allows for catching and snagging on the vessel wall during delivery. Furthermore, the large convolutions in the second meander pattern are not fully straightened out during expansion reducing rigidity and structural strength of the expanded stent. There is, further, no method of programming the stent diameter along its longitudinal axis to achieve a tapering stent design, and no method of reenforcement of stent ends or other regions is provided for.

These and other conventional stent designs suffer in varying degrees from a variety of drawbacks including: (a) inability to negotiate bends in vessels due to columnar rigidity of the unexpanded stent; (b) lack of structural strength, radial and axial lateral, of the unexpanded stent; (c) significant foreshortening of the stent during expansion; (d) limited stent length; (e) constant expanded stent diameter; (f) poor crimping characteristics; and (g) rough surface modulation of the unexpanded stent.

There is a need for a stent with sufficient longitudinal flexibility in the unexpanded state to allow for navigation through tortuous vessels. There is a further need for a stent that is structurally strong in the unexpanded state such that risk of damage or distortion during delivery is minimal. A further need exists for a stent that maintains substantially the same longitudinal length during expansion to allow greater coverage at the target site and simplify proper placement of the stent. Yet a further need exists for a stent design with sufficient longitudinal flexibility that long stents of up to 100 mm can be safely delivered through tortuous vessels. There is a need for a stent that is configured to expand to variable diameters along its length, such that a taper can be achieved in the expanded stent to match the natural taper of the target vessel. A need exists for a stent which, (i) can be crimped tightly on the expansion balloon while maintaining a low profile and flexibility, (ii) has a smooth surface modulation when crimped over a delivery balloon, to prevent catching and snagging of the stent on the vessel wall during delivery, (iii) with reenforcement rings on the ends or middle or both to keep the ends of the stent securely positioned against the vessel walls of the target blood vessel or (iv) is flexible in a non-expanded state and becomes rigid when expanded.

SUMMARY OF THE INVENTION

Accordingly an object of the present invention is to provide a scaffold for an interior lumen of a vessel.

Another object of the invention is to provide a stent which prevents recoil of the vessel following angioplasty.

A further object of the invention is to provide a stent that maintains a larger vessel lumen compared to the results obtained only with balloon angioplasty.

Yet another object of the invention is to provide a stent that reduces foreshortening of a stent length when expanded.

Another object of the invention is to provide a stent with increased flexibility when delivered to a selected site in a vessel.

A further object of the invention is to provide a stent with a low profile when crimped over a delivery balloon of a stent assembly.

Yet a further object of the invention is to provide a stent with reduce tuliping of the stent struts during delivery through the body lumen.

Another object of the invention is to provide a chain mesh stent that reduces vessel "hang up" in a tortious vessel or a vessel with curvature.

These and other objects of the invention are achieved in a stent in a non-expanded state. A first expansion column has a plurality of first expansion column slots that are formed of a plurality of first expansion struts. Substantially each first column expansion slot has a longitudinal axis. A second expansion column has a plurality of second expansion column slots that are formed of a plurality of second expansion struts. Substantially each second expansion column strut has a longitudinal axis. A first connecting strut column is formed of a plurality of first connecting struts. The first connecting strut column couples the first expansion column to the second expansion column. The first expansion column, second expansion column and the first connecting strut column form a first tubular structure with a longitudinal axis. The longitudinal axis of the first expansion column slots is non-parallel to the longitudinal axis of the first tubular structure.

In another embodiment, the slotted stent in the non-expanded state includes a first expansion column with a plurality of first expansion column slots that are formed of a plurality of first expansion struts. Substantially each first expansion column slot has a longitudinal axis. A second expansion column has a plurality of second expansion column slots that are formed of a plurality of second expansion struts. Substantially each second expansion slot has a longitudinal axis. A first connecting strut column is formed of a plurality of first connecting struts. The first connecting strut column couples the first expansion column to the second expansion column. The first expansion column, second expansion column and the first connecting strut column form a first tubular structure with a longitudinal axis and a plurality of geometric cells. At least a portion of the plurality of geometric cells are asymmetrical. The longitudinal axis of the first expansion column slots is non-parallel to the longitudinal axis of the first tubular structure.

In another embodiment, a stent assembly includes a balloon and an expandable stent positioned at an exterior of the balloon. The stent has a first expansion column with a plurality of first expansion column slots that are formed of a plurality of first expansion column struts. The first expansion column slots have a longitudinal axis. A second expansion column includes a plurality of second expansion column slots that are formed of a plurality of second expansion struts. The second expansion column slots have a longitudinal axis. A first connecting strut column is formed of a plurality of first connecting struts. The first connecting strut column couples the first expansion column to the second expansion column. The first expansion column, second expansion column and the first connecting strut column form a first tubular structure with a longitudinal axis that is non-parallel to the longitudinal axis of the first expansion column slots.

DETAILED DESCRIPTION

Figure 1:
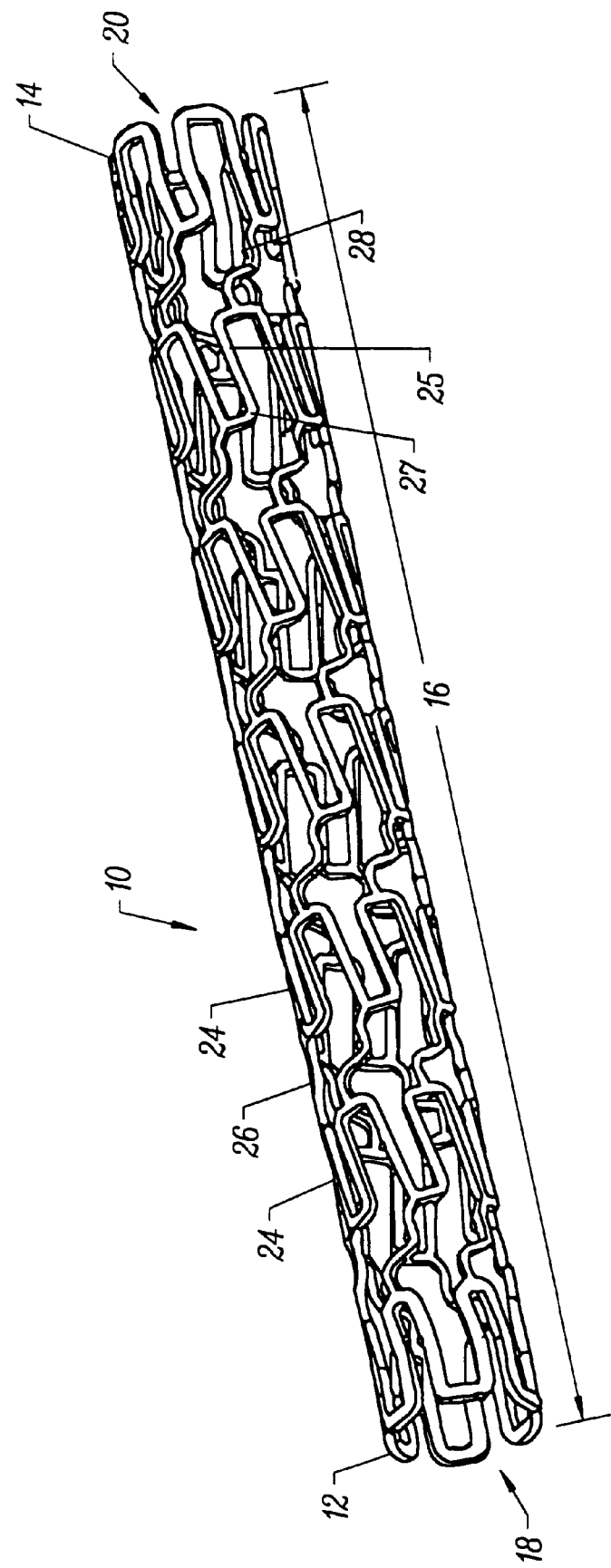
FIG. 1 is an isometric view of one embodiment of a stent in an unexpanded state with stent slots that are non-parallel to a longitudinal axis of the stent.

A first embodiment of the present invention is shown in FIGS. 1 through 4. An elongated hollow tubular stent 10 is a single prosthesis in an unexpanded state. A proximal end 12 and a distal end 14 define a longitudinal length 16 of stent 10. The longitudinal length 16 of the stent 10 can be as long as 100 mm or longer. A proximal opening 18 and a distal opening 20 connect to an inner lumen 22 of stent 10. Stent 10 can be a single piece, without any seams or welding joints or may include multiple pieces. In the expanded state, the internal diameter of stent 10 is variably enlarged without substantially fore-shortening of the length of stent 10.

Stent 10 made in proper size and scale can be used for a variety of vascular and non-vascular lumens, as well as hollow body organs. Some specific body sites include coronary vessels, coronary bypass grafts, carotid arteries, renal arteries, peripheral vessels, bile ducts, the esophagus, the urethra, the aorta and the like.

Stent 10 is constructed of two to fifty or more expansion columns 24 linked together by interspersed connecting strut columns 26. The first column on the proximal end 12 and the last column on the distal end 14 of stent 10 are modified expansion columns 24.

Each expansion column 24 is formed of a series of expansion struts 25, and joining struts 27. Expansion struts 25 are thin elongated members. When an outward external force is applied to stent 10 from the inside by an expansion balloon or other means, expansion struts 25 are reoriented such that they extend in a more circumferential direction, i.e along the surface of stent 10. Reorientation of expansion struts 25 causes stent 10 to have an expanded circumference and diameter.

Expansion struts 25 and joining struts 27 form a plurality of expansion strut pairs 30 which define an expansion column slot 32. Expansion strut pairs 30 have a closed end 34 and an open end 36. Connecting struts 28 join together expansion struts 25 of adjacent expansion strut pairs 30, such that expansion struts 25 are joined alternately at their proximal and distal ends to adjacent expansion struts 25 to form expansion columns 24.

Figure 2:
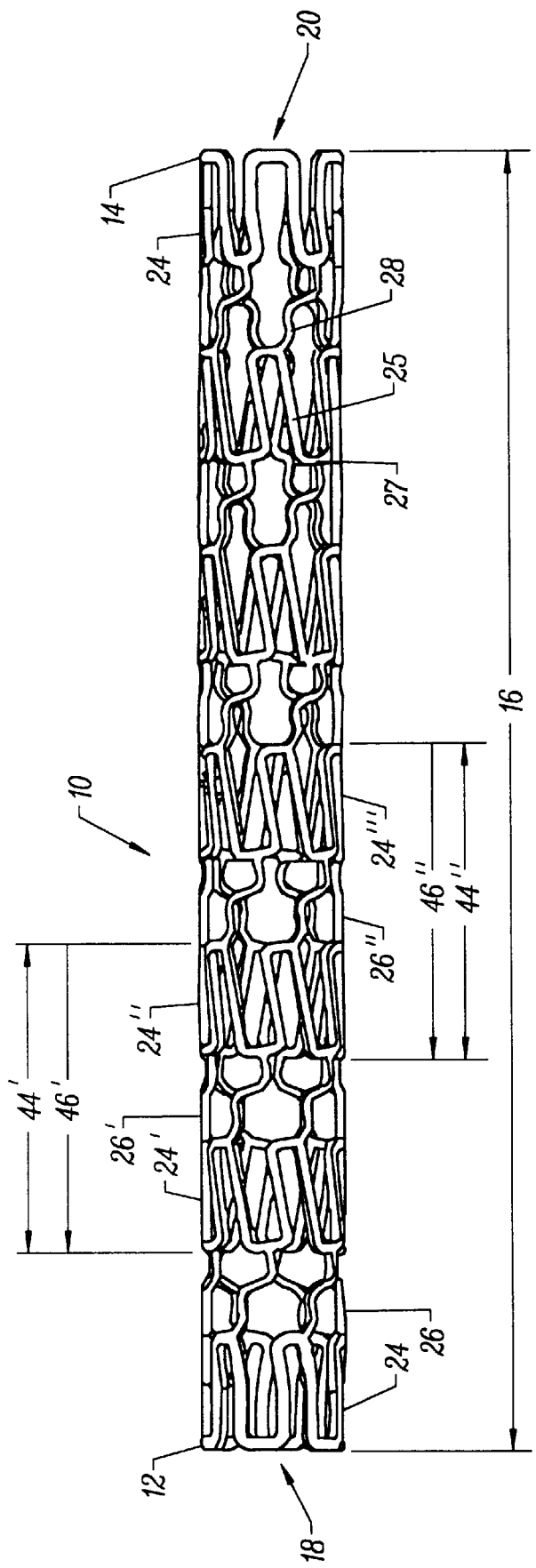
FIG. 2 is an isometric side elevation view of the stent of FIG. 1.
Figure 4:
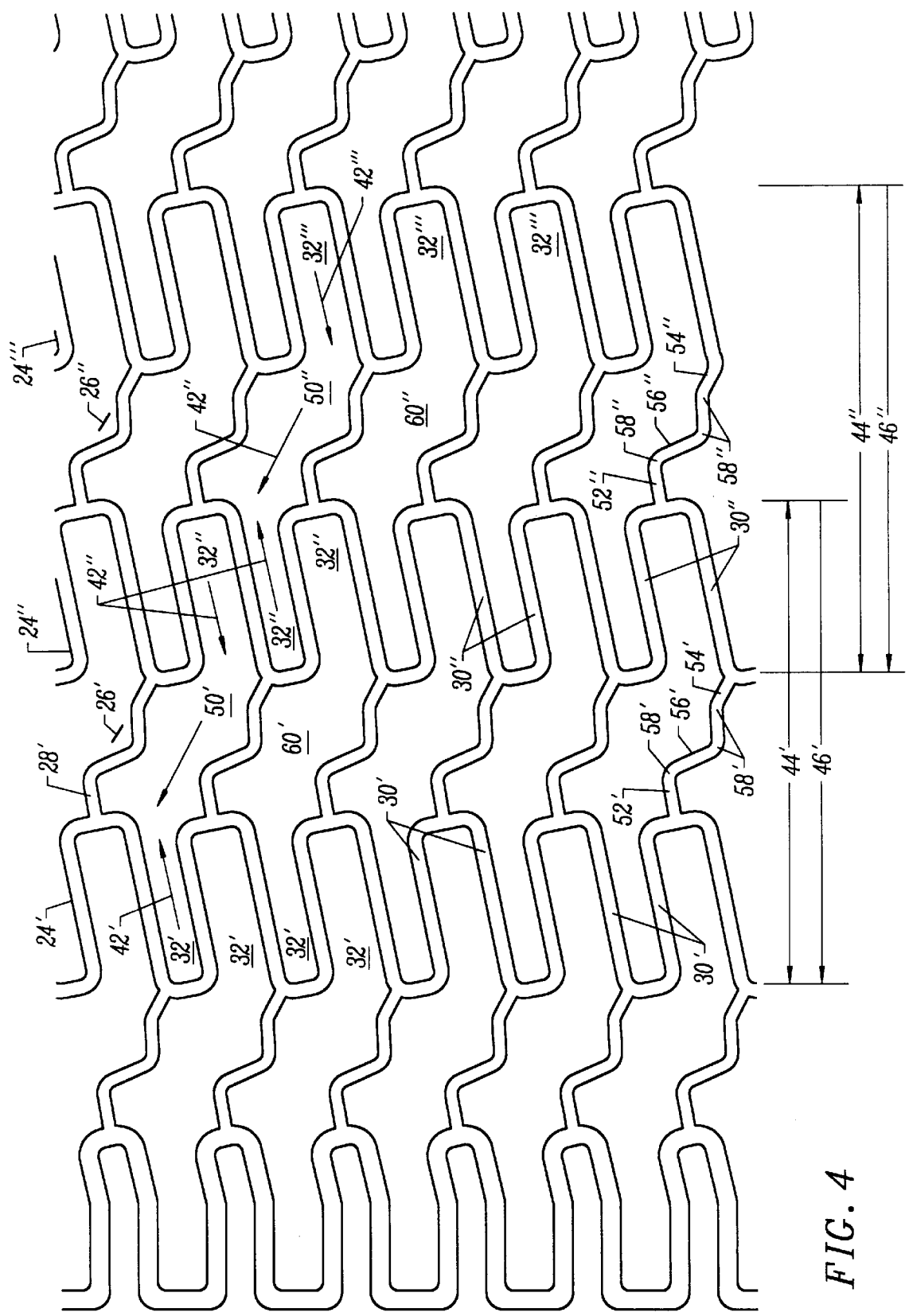
FIG. 4 is a magnified view of FIG. 3.

As illustrated more fully in FIGS. 2 and 4, a first expansion column 24' has a plurality of first expansion column slots 32' that are formed of a plurality of first expansion strut pairs 30'. Substantially each first column expansion column slot 32' has a longitudinal axis 42'. A second expansion column 24" has a plurality of second expansion column slots 32" that are formed of a plurality of second expansion strut pairs 30". Substantially each second expansion column slot 32" has a longitudinal axis 42". A first connecting strut column 26' couples the first expansion column 24' to the second expansion column 24". The width of adjacent first expansion column slots 32' are different, and the width of adjacent second expansion column slots 32" are also different. It will be appreciated that in other embodiments, the width and area of first expansion column slots 32' can be the same as second expansion column slots 32"; and adjacent first column expansion slots 32' can have the same width, as can the widths of adjacent second column expansion slots 32".

First expansion column 24', second expansion column 24" and first connecting strut column 26' form a first tubular structure 44' with a longitudinal axis 46'. Longitudinal axis 42' of first expansion column slots 32' is non-parallel to the longitudinal axis 46' of first tubular structure 44'. Second expansion column 24", second connecting strut column 26" and third expansion column 24'" form a second tubular structure 44" with a longitudinal axis 46" that is substantially the same as longitudinal axis 46'.

Connecting struts 28' of first connecting strut column 26' have a longitudinal axis 50' that is substantially parallel to a longitudinal axis 50" of connecting struts 28" of second connecting strut column 26". Connecting struts 28' and 28" extend generally in the same direction and have a "stair-step" geometric configuration. Each connecting strut 28' and 28" has a proximal portion 52' and 52", distal portion 54' and 54" and an intermediate portion 56' and 56", respectively. In the embodiment of FIGS. 1 through 4, proximal portion 52' is coupled to a non-corner (intermediate section) of an expansion strut pair 30' of first expansion column 24', and a distal portion 54' is coupled to a corner section of an expansion strut pair 30" of second expansion column 24".

Connecting struts 28' and 28" include a plurality of angled junctions 58' and 58" which increase stent 10 introduction flexibility through the body lumen. In the expanded state of stent 10, angled junctions 58' and 58" become substantially straightened out and reduce stent fore-shortening.

It will be appreciated that in other embodiments, only a portion of the adjacent connecting struts 28' or 28" include angled junctions 58' and 58", respectively.

Figure 3:
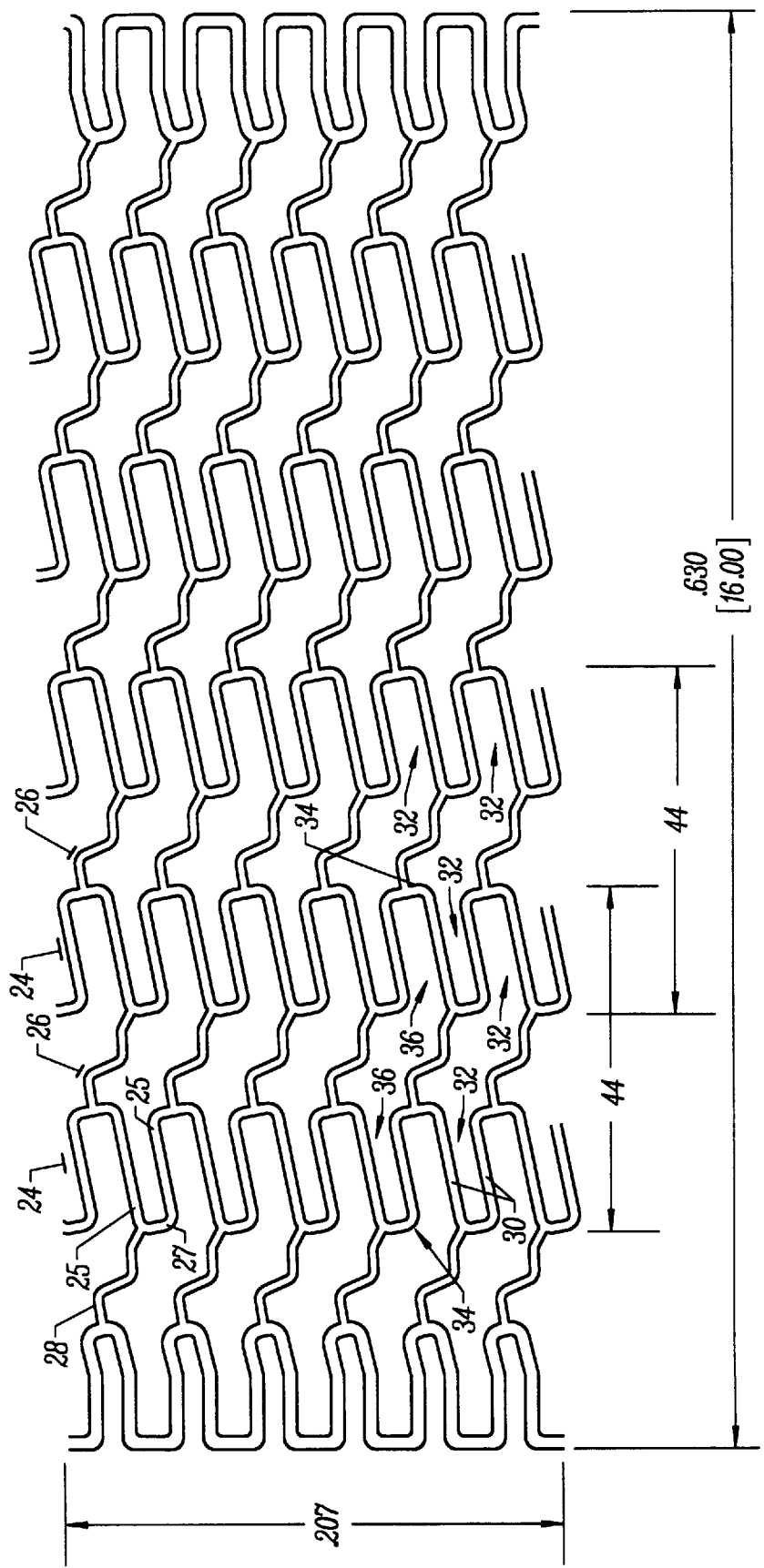
FIG. 3 is a two-dimensional, lay-out view of the stent of FIGS. 1 and 2, with the non-paralleling stent slots and the connecting struts of each connecting strut column extending substantially in the same direction.

FIG. 3 is a scale drawing of a 16 mm stent with a circumference of 0.207 inches and particularly sized for coronary applications.

Stent 10 is ideally suited for application in coronary vessels although versatility in stent 10 design allows for applications in non-coronary vessels, the aorta, and nonvascular tubular body organs.

Typical coronary vascular stents have expanded diameters that range from 2.5 to 5.0 mm. However, a stent 10 with high radial strength and fatigue tolerance that expands to a 5.0 mm diameter may have unacceptably high stent metal fraction when used in smaller diameter vessels. If the stent metal fraction is high, the chances of acute thrombosis and restenosis potential will increase. Even with the same metal fraction a smaller caliber vessel is more likely than a larger one to have a high rate of thrombosis. It is, therefore, preferred to have at least two different categories of stents 10 for coronary application; for example, small vessels stents for use in vessels with diameters from 2.5 mm to 3.0 mm, and large vessel stents for use in vessels with diameters from 3.0 mm to 5.0 mm. Thus, both small vessels and large vessels when treated with the appropriate sized stent will contain stents 10 of similar idealized metal fraction.

Stent 10 can be made using a CAM-driven laser cutting system to cut the stent pattern from a stainless steel tube. The rough-cut stent 10 is preferably electro-polished to remove surface imperfections and sharp edges. Flat sheets of suitable metal can be cut with the stent portion and rolled into a tubular shape and welded. Other methods of fabricating stent 10 can also be used such as EDM, photo-electric etching technology, or other methods. Any suitable material can be used for stent 10 including other metals and polymers so long as they provide the essential structural strength, flexibility, biocompatibility and expandability.

Stent 10 is typically at least partially plated with a radiopaque metal, such as gold, platinum, tantalum or other suitable metal, and radiopaque mark under fluoroscopy. It is preferred to plate only both ends of the stent 10 by localized plating. However, the entire stent 10 or other regions can also be plated. When plating both ends, one to three or more expansion columns 24 on each end of stent 10 are plated to mark the ends of the stent so they can be identified under fluoroscopy during the stenting procedure. By plating stent 10 only at the ends, interference of the radiopaque plating material with performance characteristics or surface modulation of the stent frame is minimized. Additionally the amount of plating material required is reduced, lowering the material cost of the plating metal, such as gold.

After plating, stent 10 is cleaned, typically with detergent, saline and ultrasonic means that are well-known in the art. Stents 10 are then inspected for quality control, assembled with the delivery balloon catheter, and properly packaged, labeled, and sterilized.

Stent 10 can be modified for larger vessels such as renal arteries, the aorta, as well as any tubular body structure such as urethra, and the bile duct, as well as any other body lumens.

First expansion column 24', second expansion column 24" and first connecting strut column 26' form first tubular structure 44' which is made of a plurality of asymmetric cells 60'. Second expansion column 24", third expansion column 24'" and second connecting strut column 26" form second tubular structure 44" which is also made of a plurality of asymmetric cells 60". Cells 60' and 60" have approximately the same area. A cell 60' in first tubular structure 44' is laterally offset from a corresponding adjacent cell 60" in second tubular structure 44".

Figure 5:
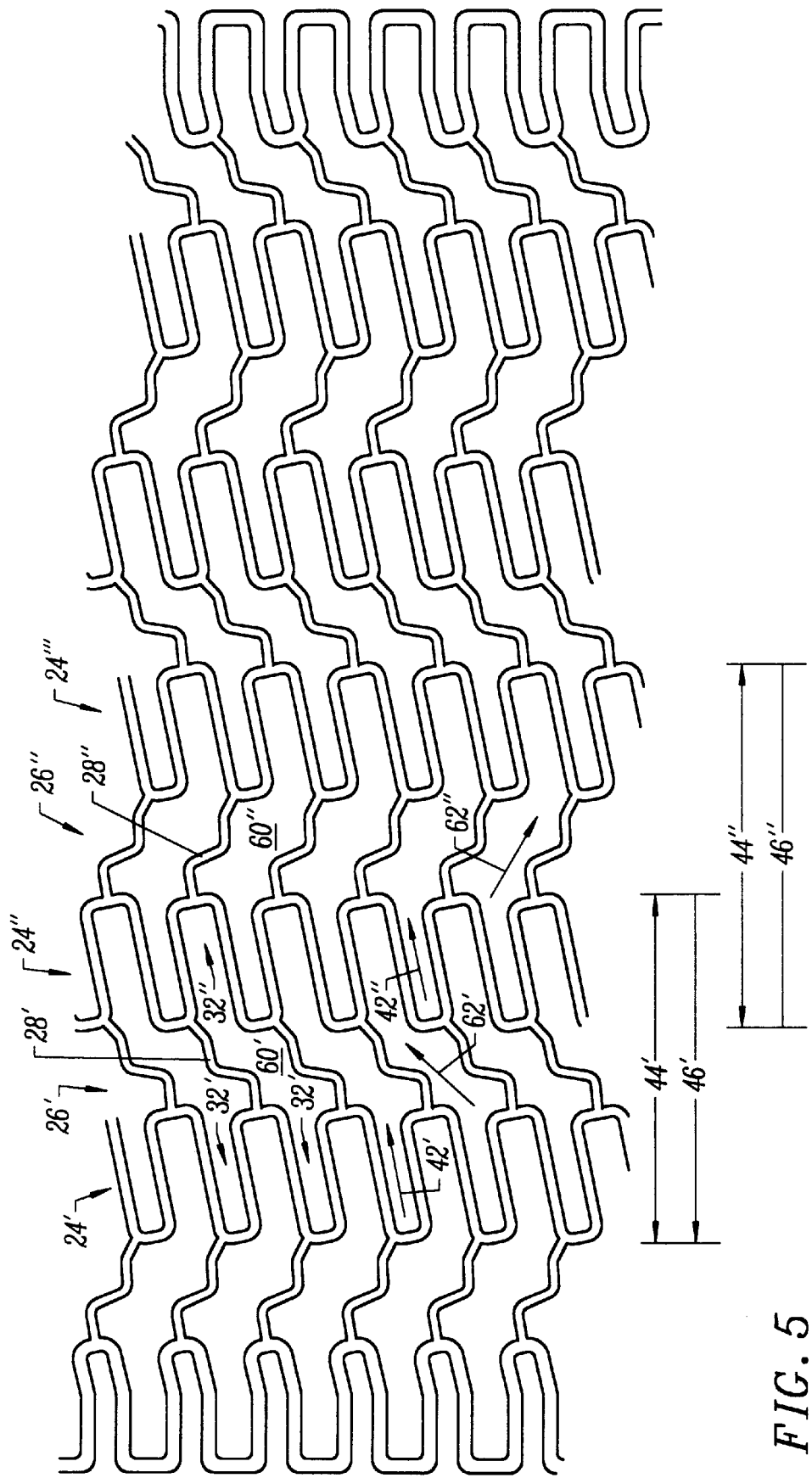
FIG. 5 is another embodiment of a stent in two-dimensional, lay-out view of an unexpanded stent with slots that are non-parallel to the longitudinal axis of the stent, and the connecting struts of a first connecting strut column extend substantially in one direction while the connecting struts of an second adjacent connecting strut column extend in a different direction, and each direction of the first and second connecting struts are non-parallel to the longitudinal axis of the stent.
Figure 6:
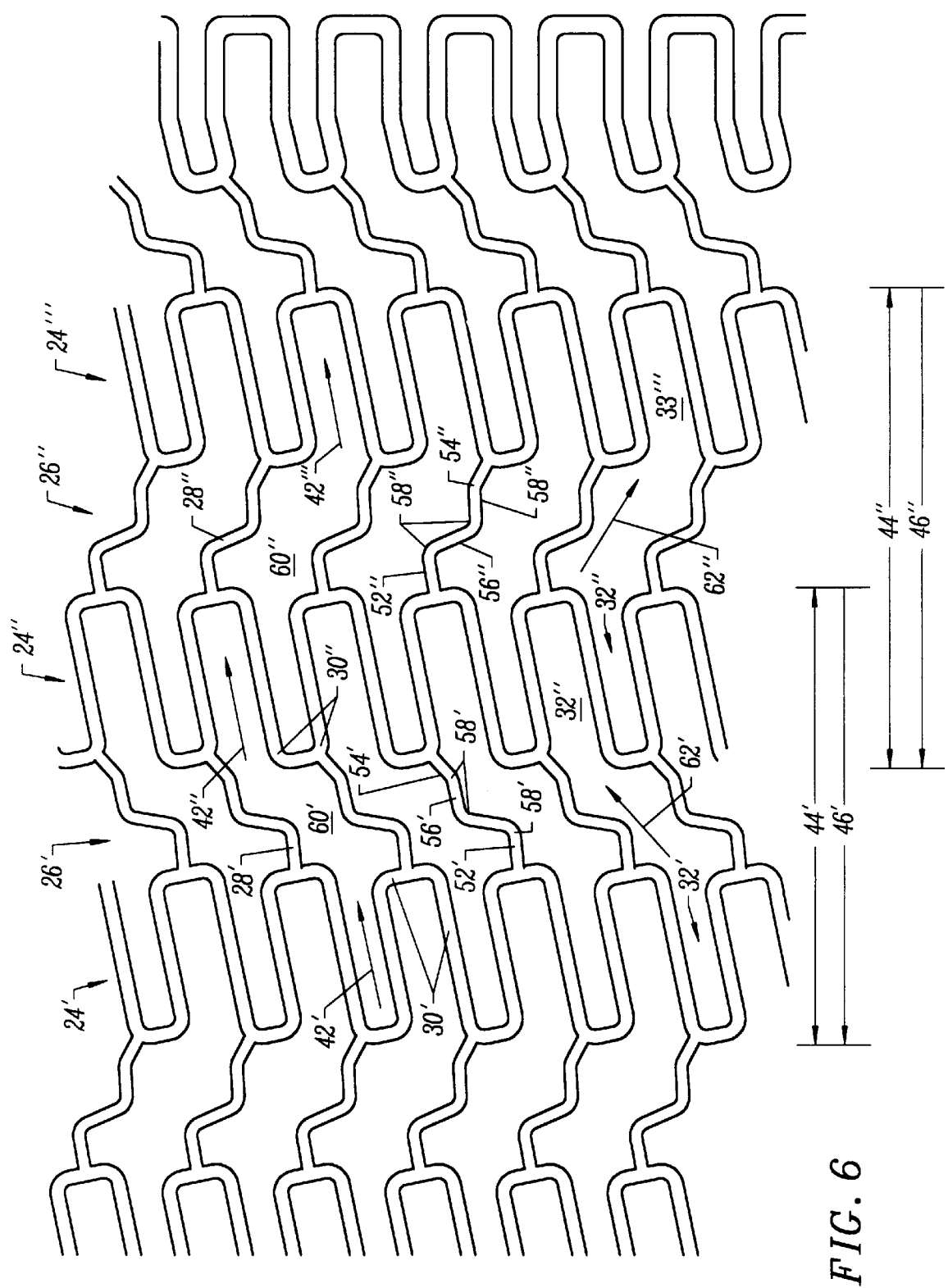
FIG. 6 is a magnified view of FIG. 5.

Another embodiment of stent 10 is illustrated in FIGS. 5 and 6. In this embodiment, connecting struts 28' in first connecting strut column 26' extend in an upward direction 62' while connecting struts 28" in adjacent second connecting strut column 26" extend in a downward direction 62". In this embodiment, there is more balanced flexibility during the delivery phase of stent 10 to the desired site. By arranging the axes 62' and 62" of connecting struts 28' and 28" in an alternating and generally opposing direction, any potential of axial warping of the stent 10 is prevented. The expansion strut pairs 30' and 30" are parallel to each other. The axes 42' an 42" of expansion column slots 32' and 32" are also parallel to each other, but they are nonparallel to the longitudinal axes 46' and 46" of stent 10. In the embodiment illustrated in FIGS. 5 and 6, cells 60' and 60" are asymmetrical.

Figure 7:
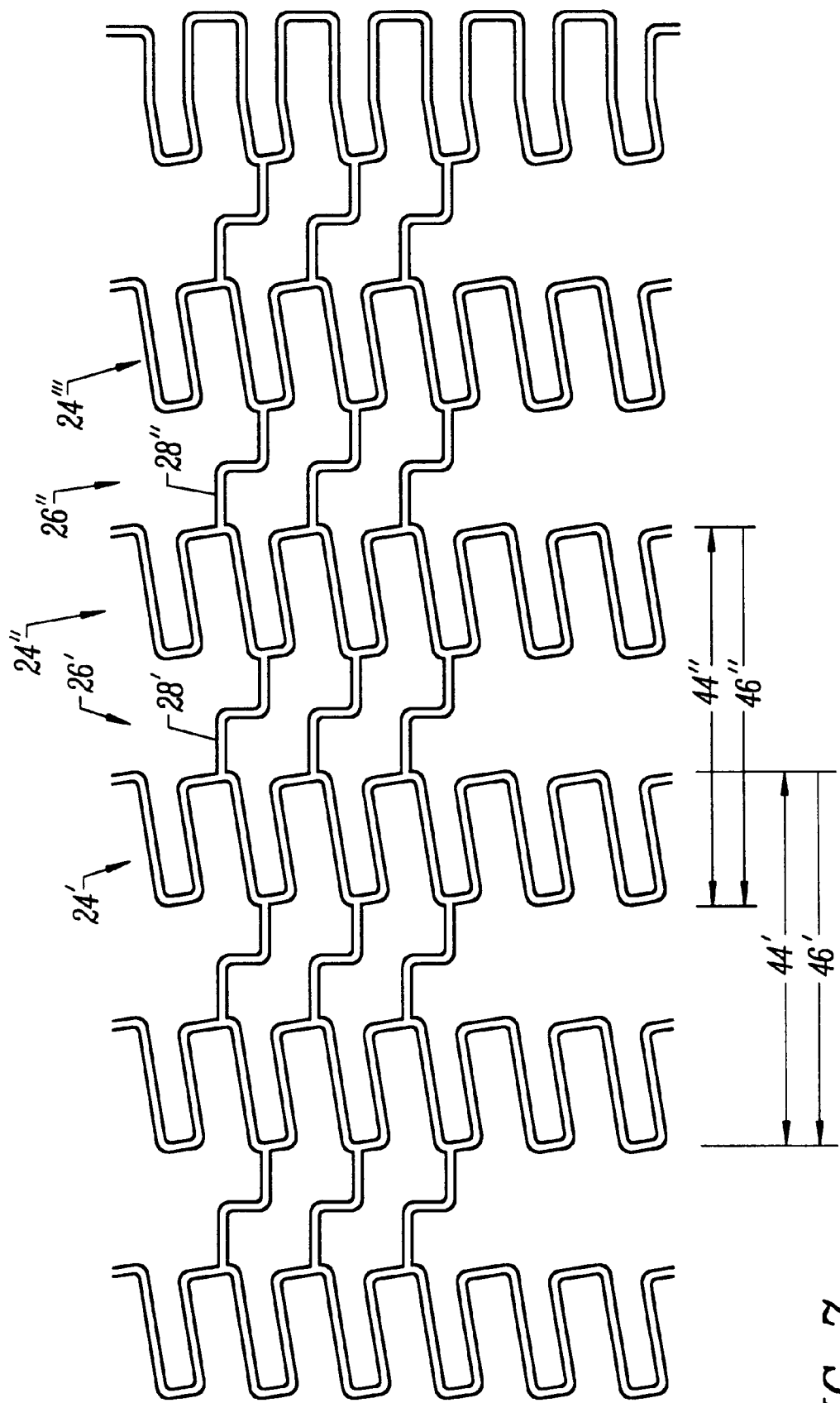
FIG. 7 is a two-dimensional, lay-out view of another embodiment of an unexpanded stent with slots that are non-parallel to the longitudinal axis of the stent, the stent includes stair-step connecting struts with sections that are substantially parallel to the longitudinal axis of the stent.
Figure 8:
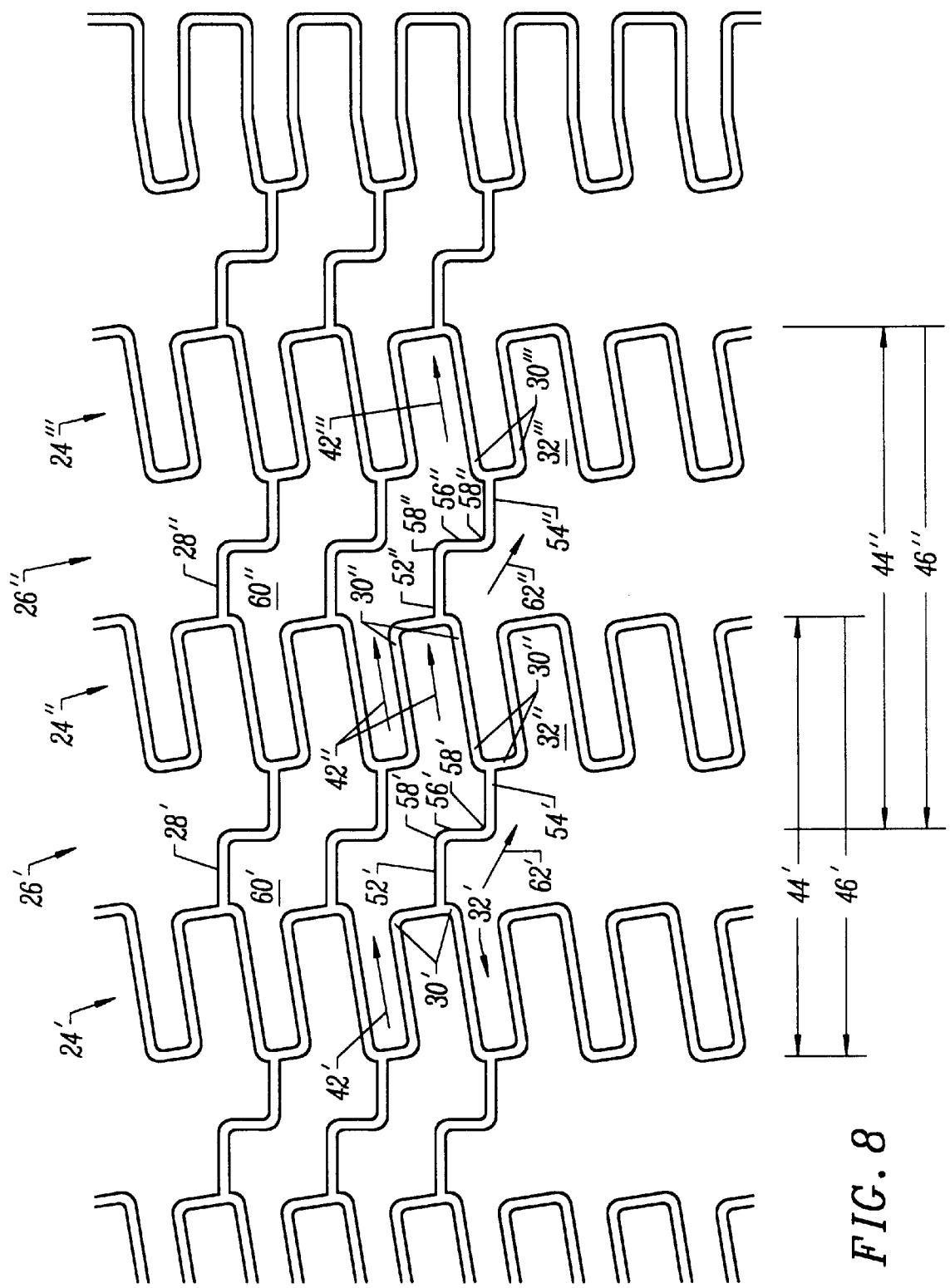
FIG. 8 is a magnified view of FIG. 7.

In the embodiment illustrated in FIGS. 7 and 8, proximal portion 52' of connecting strut 28' is coupled to a corner of an expansion strut pair 30' of first expansion column 24', a distal portion 54' of connecting strut 28' is coupled to a corner section of an expansion strut pair 30" of second expansion column 24"; proximal portion 52" of connecting strut 28" is coupled to a corner of an expansion strut pair 30" of second expansion column 24", and a distal portion 54" is coupled to a corner section of an expansion strut pair 30"'. Connecting struts 28' and 28" have one stair-step. Proximal sections 52' and 52", and distal sections 54' and 54" are substantially parallel to longitudinal axes 46' and 46", respectively. This embodiment is an alternative in connection strut configuration.

Figure 9:
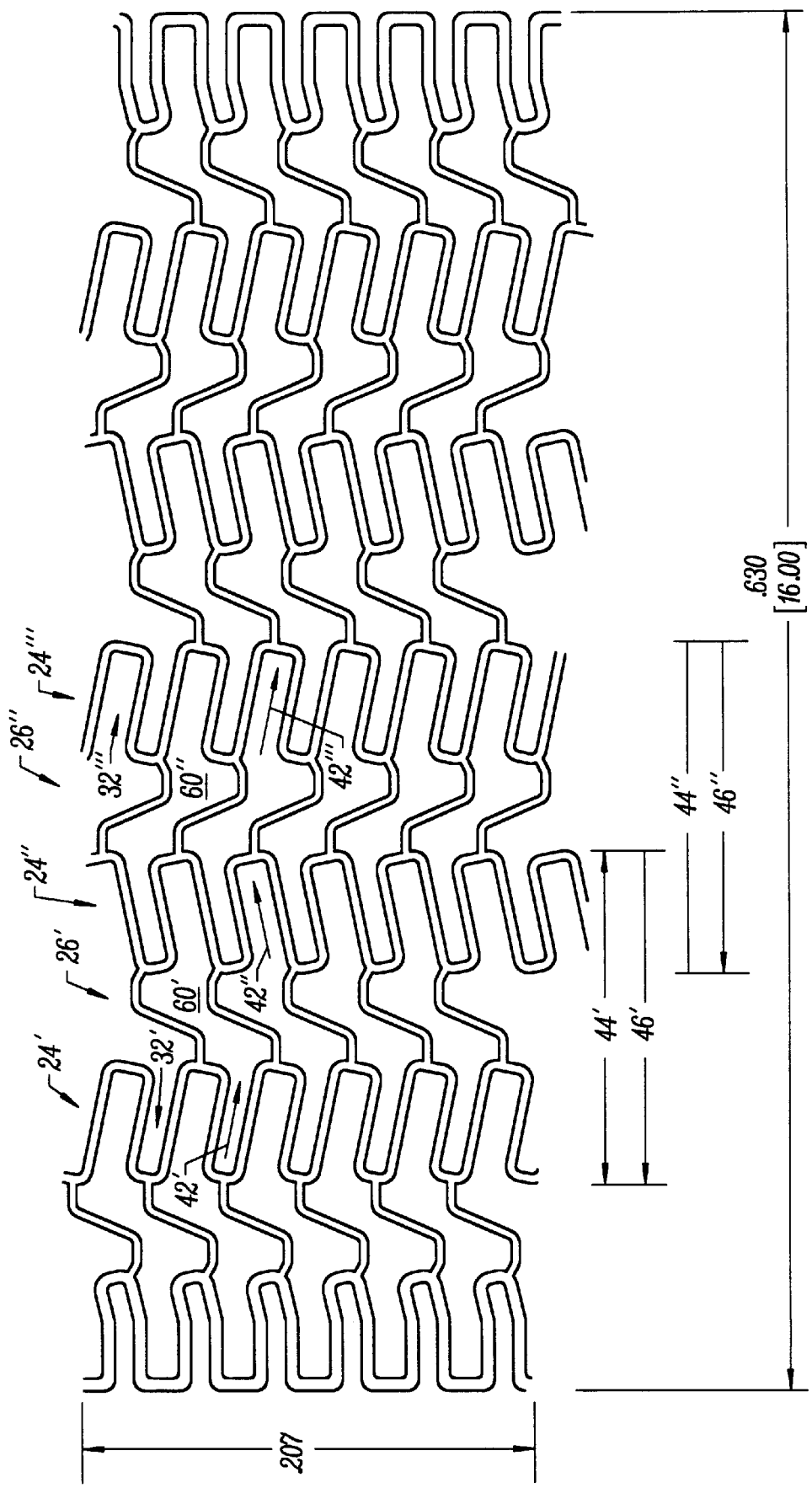
FIG. 9 is a two-dimensional, lay-out view of another embodiment of an unexpanded stent with slots that are non-parallel to the longitudinal axis of the stent; the slots of a first expansion column are non-parallel to the slots of a second expansion column, the connecting struts of a first connecting strut column extend substantially in one direction while the connecting struts of an second adjacent connecting strut column extend in a different direction, and of the first and second connecting struts are non-parallel to the longitudinal axis of the stent.
Figure 10:
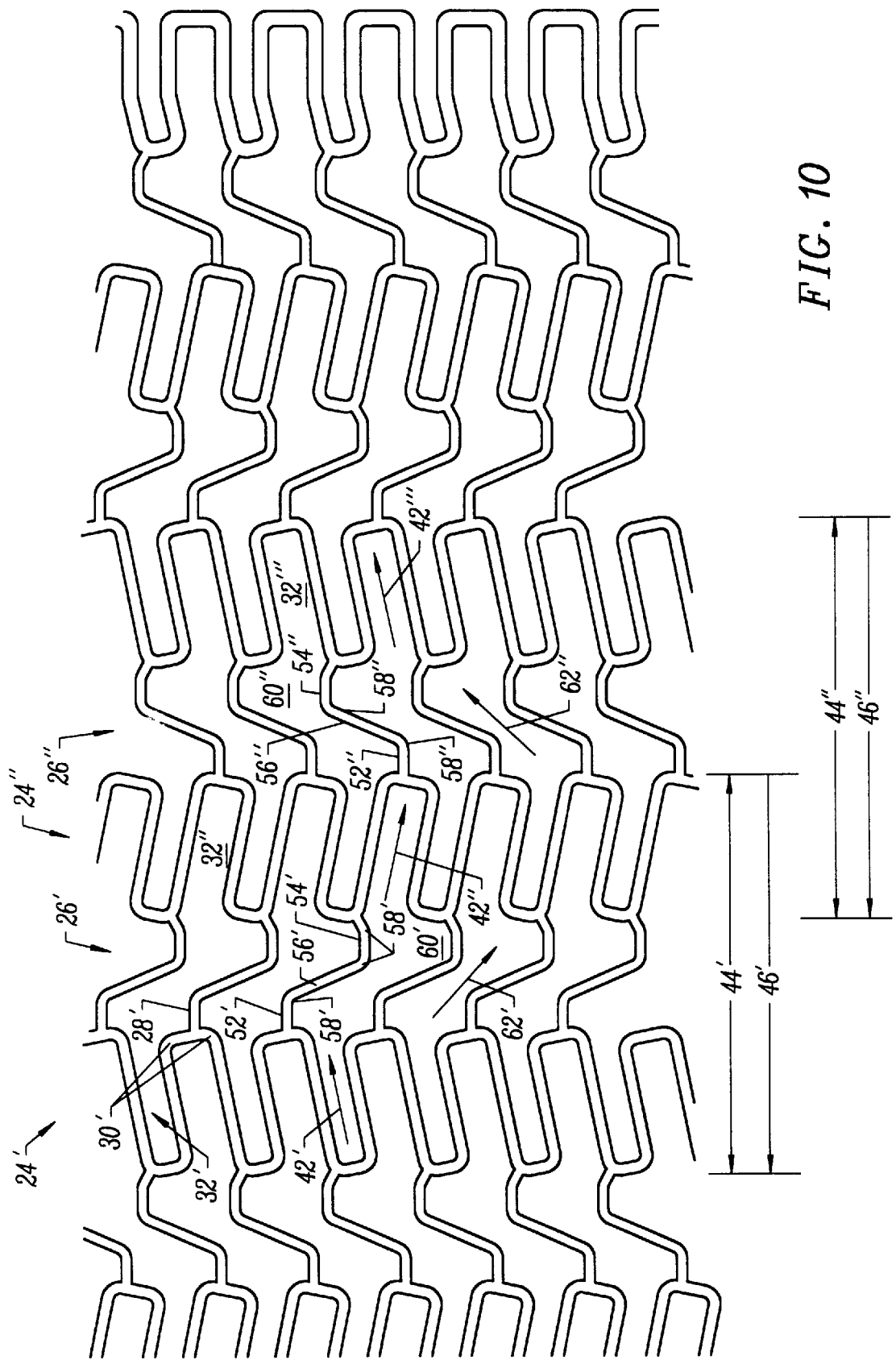
FIG. 10 is a magnified view of FIG. 9.

Referring now to the embodiment of FIGS. 9 and 10, longitudinal axis 42' of first expansion column slot 32' is non-parallel to longitudinal axis 42" of slot 32" but is parallel to longitudinal axis 42"' of slot 32"'. Proximal portion 52' of connecting strut 28' is coupled to a non-corner of an expansion strut pair 30' of first expansion column 24' and distal portion 54' of connecting strut 28' is coupled to a corner section of an expansion strut pair 30" of second expansion column 24". Connecting struts 28' in first connecting strut column 26' extend in a downward direction 62' while connecting struts 28" in adjacent second connecting strut column 26" extend in an upward direction 62". Cells 60' and 60" have asymmetrical geometric configuration. The axes 42' and 42" of slots 32' and 32" are non-parallel to each other, and they are non-parallel to the axes 46' and 46" of stent 10. The expansion strut pairs 30' and 30" have two elongated struts that are parallel to each other.

Figure 11:
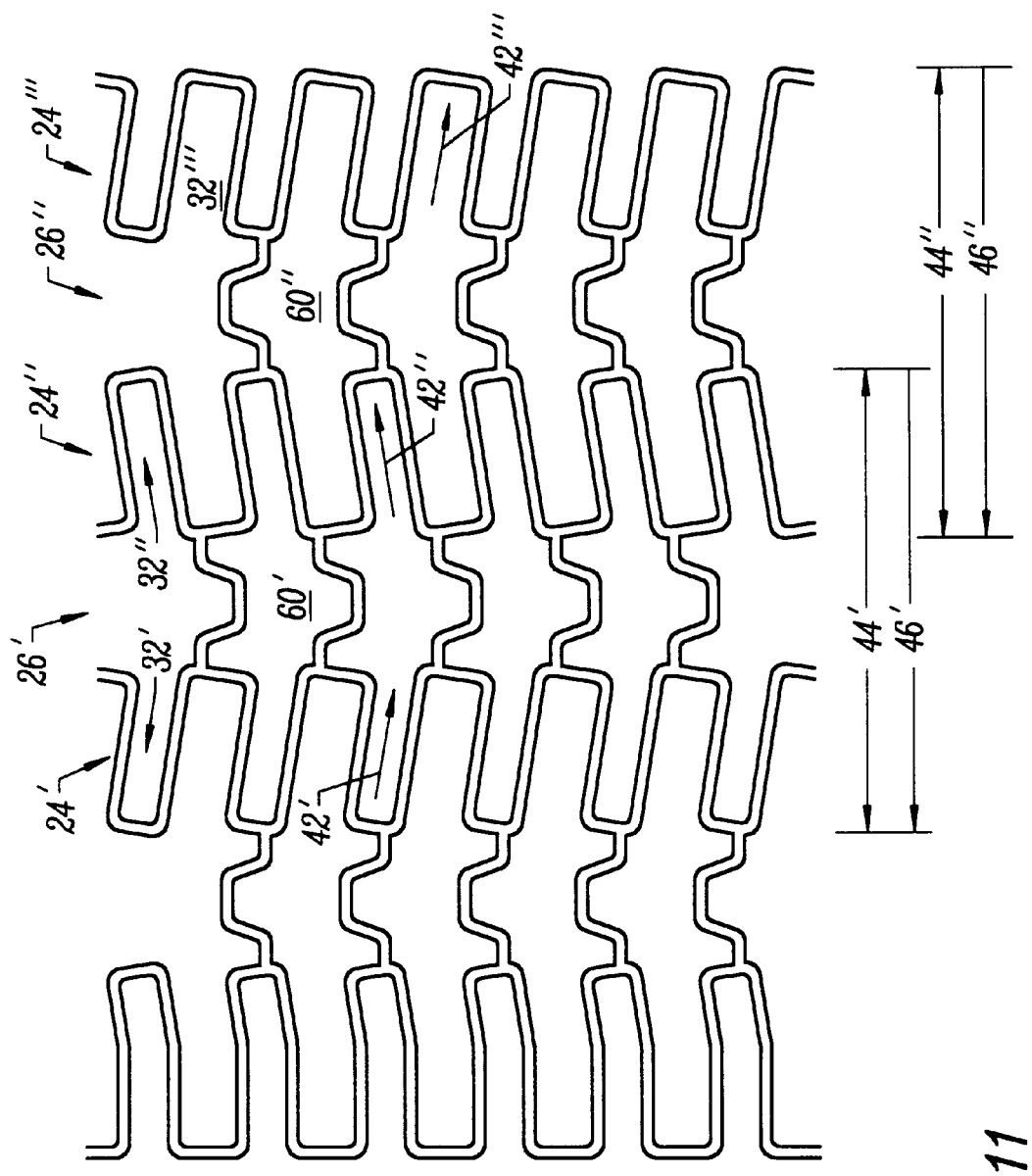
FIG. 11 is a two-dimensional, lay-out view of yet another embodiment of an unexpanded stent with slots that are non-parallel to the longitudinal axis of the stent; the slots of a first expansion column are non-parallel to the slots of a second expansion column, sections of the connecting struts are parallel to the longitudinal axis of the stent.
Figure 12:
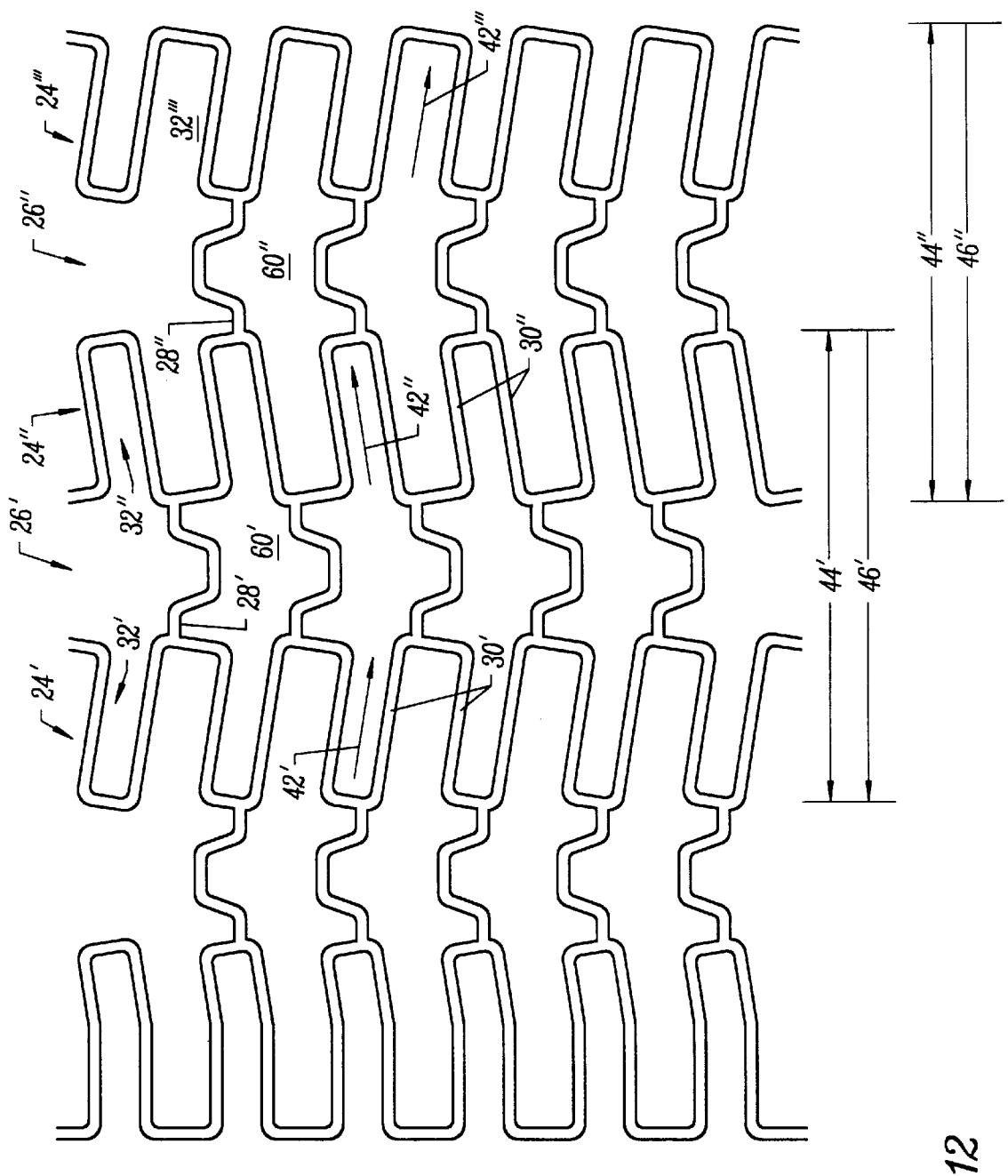
FIG. 12 is a magnified view of FIG. 11.

In the embodiment of FIGS. 11 and 12, longitudinal axis 42' of first expansion column slot 32' is non-parallel to longitudinal axis 42" of slot 32". The expansion strut pairs 30' and 30" have elongated paralleling struts forming the slots 32' and 32". The axes 42' and 42" of slots 32' and 32" are non-parallel to the longitudinal axis 46' and 46" of stent 10. Cells 60' and 60" are symmetrical. Connecting struts 28' and 28" have a symmetrical "saddle" geometric shape with five sections. This symmetrical "saddle" shape of connective struts 28' and 28" provides uniform flexibility in the "north and south" directions perpendicular to the longitudinal axes 46' and 46" of stent 10. When stent 10 is in an expanded state, the saddle straightens out and thus reduces foreshortening.

Figure 13:
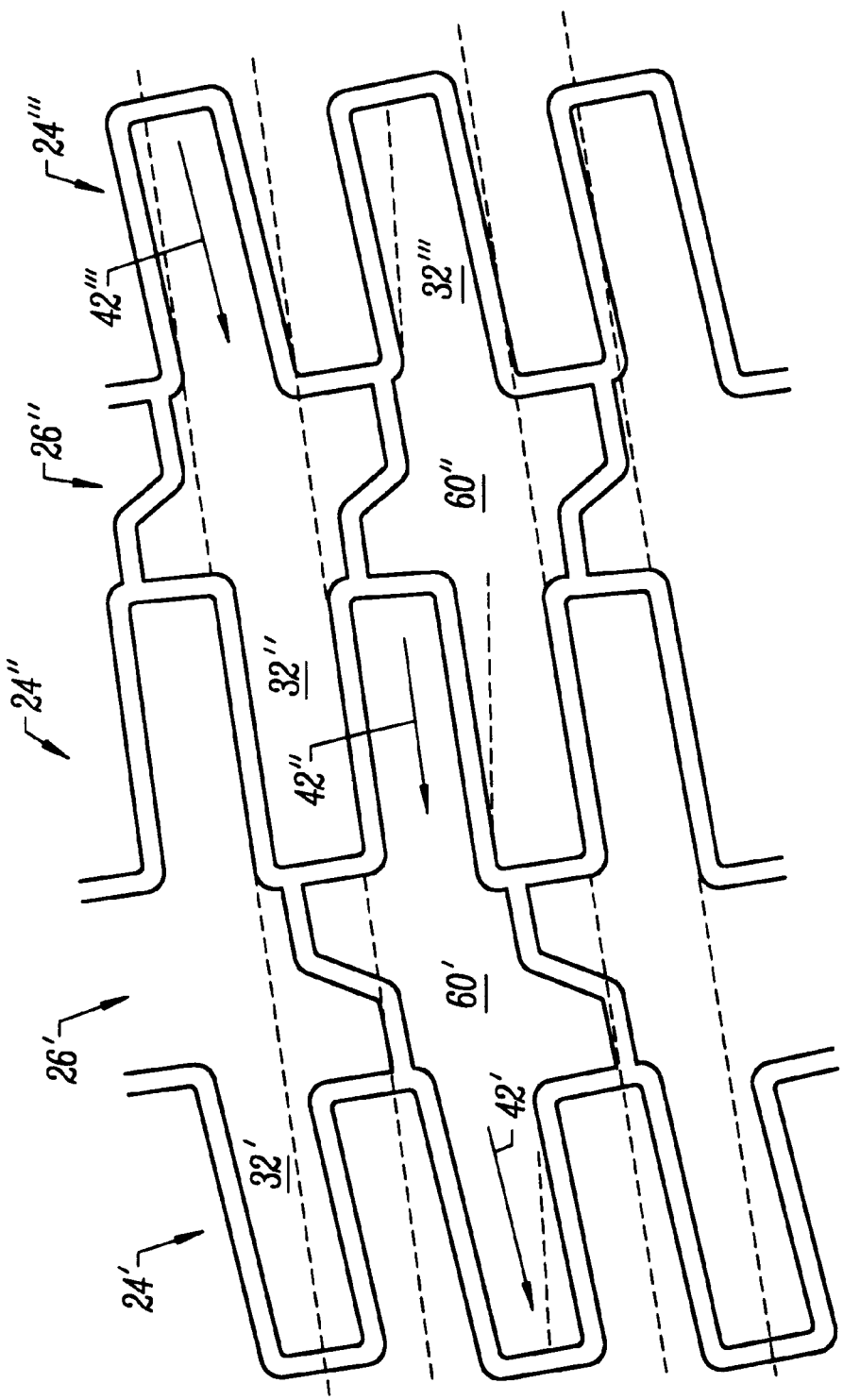
FIG. 13 is a two-dimensional, lay-out view of an unexpanded stent where the slots of a first expansion column are parallel to the slots of a third expansion column but are not parallel to the slots of a second expansion column.

FIG. 13 illustrates an embodiment of stent 10 where longitudinal axis 42' is non-parallel to the longitudinal axis 46' of the first tubular structure 44'. Longitudinal axis 42" is non-parallel to the longitudinal axis 46", and the longitudinal axis 42' is non-parallel to the longitudinal axis 42".

First tubular structure 44' is formed of first closed cells 60' and second tubular structure is formed of second closed cells 60" which are asymmetrical. First closed cells 60' are non-mirror images of second closed cells 60". First and second connecting struts 28' and 28" each have a stair-step configuration.

Figure 14:
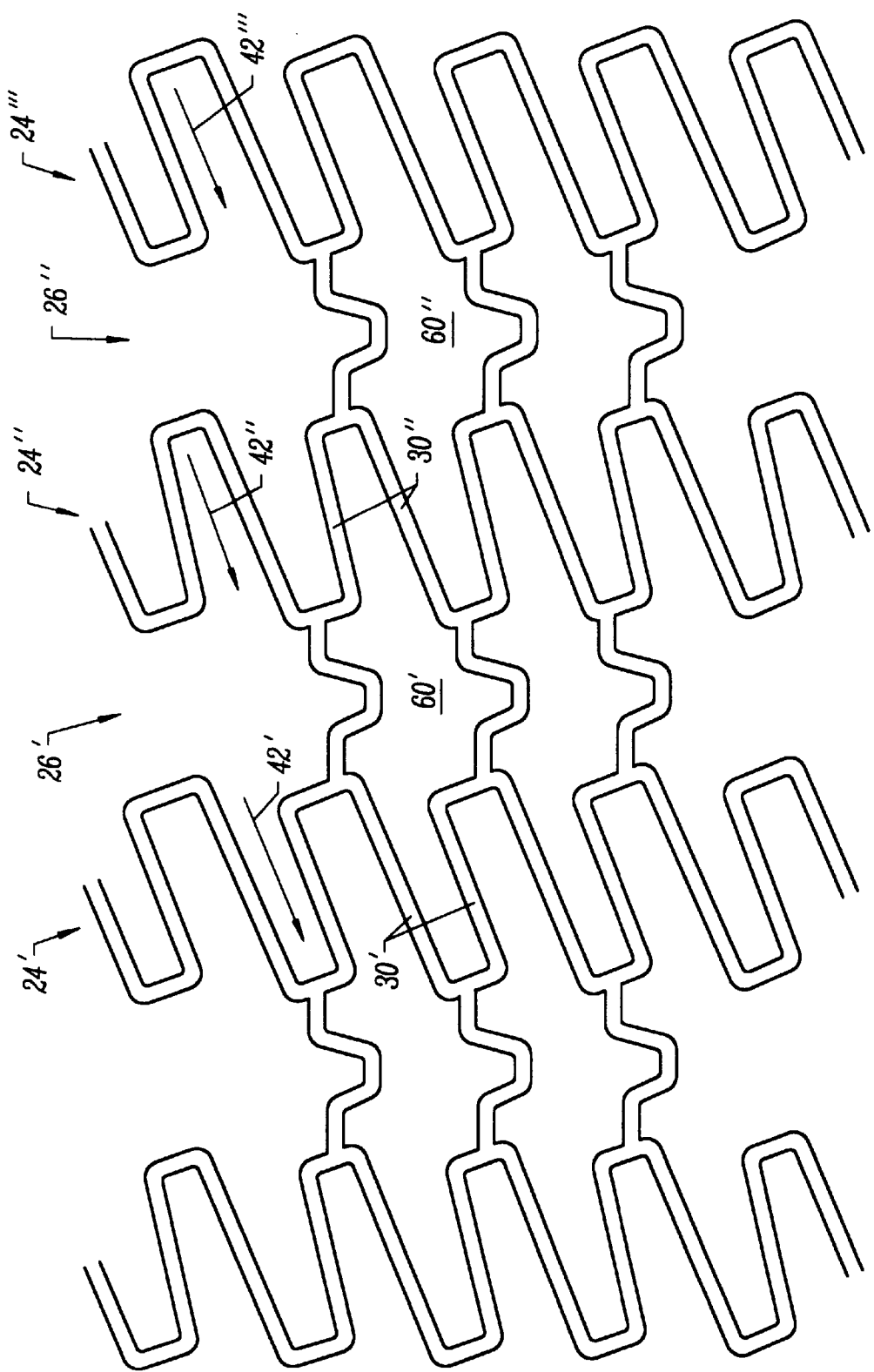
FIG. 14 is a two-dimensional, lay-out view of an unexpanded stent where the slots of the second expansion column are formed of non-parallel expansion strut pairs.

FIG. 14 illustrates another embodiment of stent 10 where longitudinal axis 42' is non-parallel to longitudinal axis 46'. Longitudinal axis 42' is non-parallel to longitudinal axis 46". First expansion column strut pairs 30' are parallel, second expansion column strut pairs 30" are non-parallel and third expansion column strut pairs 30"' are parallel. First and second closed cells 60' and 60" are asymmetric cells. First closed cells 60' have different geometric shapes than second closed cells 60".

In the embodiments of the present invention, when stent 10 is expanded, expansion columns 24' and 24" become circumferentially stretched, enlarging the space between connecting struts 28' and 28". The interlinking of expansion columns 24' and 24" by connecting struts 28' that have been straightened through the expansion process provides stent 10 a high radial support strength. When expanded, the entire stent 10 is unitized into a continuous chain mesh of stretched expansion columns 24', 24", 24"', and so on with connecting strut columns 26', 26" and so on, forming interlocking cells 60', 60" and continuing thereafter, which resists collapse both axially and radially. When stent 10 is expanded it has increased rigidity and fatigue tolerance.

In addition, efficient bending and straightening of connecting struts 28 and the like at angled junctions 58 allows increased stent 10 longitudinal flexibility during delivery phase. For stent 10 to bend longitudinally, at least some of connecting struts 28 are forced to bend in their tangent plane. The tangent plane of a specific connecting strut 28 refers to the plane substantially tangent to the cylindrical surface of the stent at that connecting strut 28. Angled junctions 58 provide connecting struts 28 a flexible joint about which to more easily bend increasing longitudinal flexibility of the stent.

In one embodiment, when fully expanded, stent 10 has an internal diameter of up to 5.0 mm, while maintaining an acceptable radial strength, fatigue tolerance and fore shortening.

The crimped stent outer diameter can be as small as 1.0 mm or less depending on the condition of the underlying delivery balloon profile; A small crimped outer diameter is especially important if stent delivery is to be attempted without predilation of the target site. When stent 10 is optimally crimped over the delivery balloon, the surface of crimped stent 10 is smooth allowing for no snagging of stent struts during either forward or backward movement through a vessel or other body lumen.

Along with the use of a tapered diameter stent 10, a matching tapered balloon catheter would ideally be made for delivery and deployment of tapered diameter stent 10. The method of using a tapered matching balloon catheter with a tapered diameter stent is within the scope of the present invention. Furthermore, the tapered balloon could be curved lengthwise to match the tapered diameter stents within the scope of the present invention.

Using a tapered balloon to expand a non-tapered stent 10 will also achieve a tapered expanded stent 10. However, since no metal is removed from stent 10, stent 10 is tapered as a result of incomplete expansion. Stent 10 will therefore have increased metal fraction at the tapered end resulting in increased risk of acute thrombosis. Metal fraction is the proportion of the surface of the expanded stent 10 covered by the stent strut material. Shortening expansion struts 25 provides a tapered expanded stent 10 with substantially constant metal fraction along its length.

Figure 15:
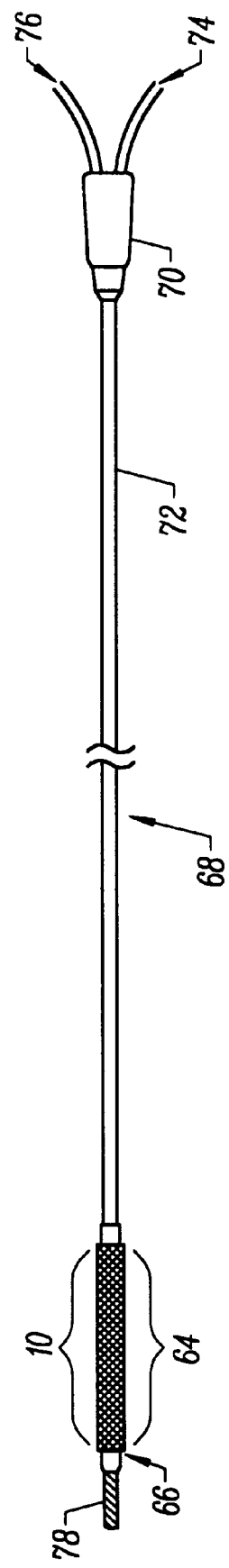
FIG. 15 is a perspective of a stent delivery system.

The stent can be marketed as stand alone or as a premounted delivery balloon catheter assembly as shown in FIG. 15. Stent 10 is crimped over a folded balloon 64 at the distal end 66 of a delivery balloon catheter assembly 68. The assembly 68 includes a proximal end adapter 70, a catheter shaft 72, a balloon channel 74, a guidewire channel 76, a balloon 64, and a guidewire 78. Balloon 64 can be tapered in an expanded state, be curved from a proximal end to a distal end in the expanded state. Additionally stent 10 can be non-tapered or tapered in the expanded state.

Typically the guidewire 78 is inserted into the vein or artery and advanced to the target site. The catheter shaft 72 is then forwarded over the guidewire 78 to position the stent 10 and balloon 64 into position at the target site. Once in position the balloon 64 is inflated through the balloon channel 74 to expand the stent 10 from a crimped to an expanded state. In the expanded state, the stent 10 provides the desired scaffolding support to the vessel. Once the stent 10 has been expanded, the balloon 64 is deflated and the catheter shaft 72, balloon 64, and guidewire 78 are withdrawn from the patient.

The stent of the present invention can be made as short as less than 10 mm in length or as long as 100 mm or more. If long stents are to be used, however, matching length delivery catheter balloons will typically be needed to expand the stents into their deployed positions. Long stents, depending on the target vessel, may require curved long balloons for deployment. Curved balloons which match the natural curve of a blood vessel reduce stress on the blood vessel during stent deployment. This is especially important in many coronary applications which involve stenting in curved coronary vessels. The use of such curved balloons is within the scope of the present invention.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A stent in a non-expanded state, comprising:
a first expansion column including a plurality of first expansion column slots formed of a plurality of first expansion struts, each of a first expansion strut being coupled to an adjacent first expansion strut by a substantially linear joining strut, the first expansion column slots having a longitudinal axis;
a second expansion column including a plurality of second expansion column slots formed of a plurality of second expansion struts, each of a second expansion strut being coupled to an adjacent second expansion strut by a substantially linear joining strut, the second expansion column slots having a longitudinal axis; and
a first connecting strut column formed of a plurality of first connecting struts, the first connecting strut column coupling the first expansion column to the second expansion column, wherein the first expansion column, the second expansion column and the first connecting strut column form a first tubular structure with a longitudinal axis, and the longitudinal axis of the first expansion column slots is non-parallel to the longitudinal axis of the first tubular structure.

2. The stent of claim 1, wherein the longitudinal axis of the second expansion slots is non-parallel to the longitudinal axis of the first tubular structure.

3. The stent of claim 1, wherein the longitudinal axis of the slots in the first expansion column is parallel to the longitudinal axis of the slots in the second expansion column.

4. The stent of claim 1, wherein at least one first connecting strut connects the first expansion column to the second expansion column.

5. The stent of claim 1, wherein a width of a first expansion column slot of the first expansion column is different from a width of a second adjacent expansion column slot of the first expansion column.

6. The stent of claim 1, wherein at least a portion of the substantially linear joining struts in the first and second expansion columns has a curved proximal end.

7. The stent of claim 1, wherein at least a portion of the substantially linear joining struts in the first and second expansion columns has a curved distal end.

8. The stent of claim 1, wherein at least a portion of the substantially linear joining struts in the first and second expansion columns has a curved proximal end and a curved distal end.

9. The stent of claim 1, wherein a longitudinal axis of the first connecting struts of the first connecting strut column is non-parallel to the longitudinal axis of the first tubular structure.

10. A slotted stent in a non-expanded state, comprising:

a first expansion column including a plurality of parallel first expansion column slots formed of a plurality of first expansion struts, the first expansion column slots having a longitudinal axis;

a second expansion column including a plurality of parallel second expansion column slots formed of a plurality of second, expansion struts, the second expansion column slots having a longitudinal axis; and a first connecting strut column formed of a plurality of first connecting struts, the first connecting strut column coupling the first expansion column to the second expansion column, wherein the first expansion column, the second expansion column and the first connecting strut column form a first tubular structure with a longitudinal axis and a plurality of closed geometric cells formed by adjacent first expansion struts, adjacent second expansion struts and adjacent first connecting struts, at least a portion of the plurality of closed geometric cells being asymmetrical closed geometric cells, the longitudinal axis of the first expansion column slots being non-parallel to the longitudinal axis of the first tubular structure.

11. The stent of claim 10, wherein a longitudinal axis of the first connecting struts of the first connecting strut column is non-parallel to the longitudinal axis of the first tubular structure.

12. The stent of claim 10, wherein the longitudinal axis of the first expansion column slots is parallel to the longitudinal axis of the second expansion column slots.

13. The stent of claim 10, wherein the longitudinal axis of the second expansion slots is non-parallel to the longitudinal axis of the first tubular structure.

14. The stent of claim 10, wherein at least one first connecting strut connects the first expansion column to the second expansion column.

15. The stent of claim 10, wherein a width of a first expansion column slot of the first expansion column is different from a width of a second adjacent expansion column slot of the first expansion column.

16. A stent assembly, comprising:

a balloon; and an unexpanded stent mounted at an exterior of the balloon, the stent including a first expansion column including a plurality of first expansion column slots formed of a plurality of first expansion struts, the first expansion column slots having a longitudinal axis, each of a first expansion strut being coupled to an adjacent first expansion strut by a substantially linear joining strut;

a second expansion column including a plurality of second expansion column slots formed of a plurality of second expansion struts, the second expansion column slots having a longitudinal axis each of a second expansion strut being coupled to an adjacent second expansion strut by a substantially linear joining strut;

a first connecting strut column formed of a plurality of first connecting struts, the first connecting strut column coupling the first expansion column to the second expansion column, wherein the first expansion column, the second expansion column and the first connecting strut column form a first tubular structure with a longitudinal axis that is non-parallel to the longitudinal axis of the first expansion column slots prior to the stent being mounted on the balloon.

17. The stent assembly of claim 16, wherein the longitudinal axis of the second expansion slots is non-parallel to the longitudinal axis of the first tubular structure.

18. The stent assembly of claim 16, wherein at least one first connecting strut connects the first expansion column to the second expansion column.

19. The stent assembly of claim 16, wherein the balloon has a tapered geometry in an expanded state.

20. The stent assembly of claim 16, wherein the balloon is curved extending from a proximal end and a distal end in an expanded state.

* * * * *